US006687528B2

(12) United States Patent
Gupta et al.

(10) Patent No.: US 6,687,528 B2
(45) Date of Patent: Feb. 3, 2004

(54) ANALYSIS OF CARDIC MR RELAXATION TIME IMAGES WITH APPLICATION TO QUANTIFYING MYOCARDIAL PERFUSION RESERVE INDEXES

(75) Inventors: Sandeep N. Gupta, Baltimore, MD (US); Garth M. Beache, Baltimore, MD (US); Daniel A. Herzka, Silver Spring, MD (US)

(73) Assignees: GE Medical Systems Global Technology Company LLC, Waukesha, WI (US); John Hopkins University, Baltimore, MD (US)

( * ) Notice: Subject to any disclaimer, the term of this patent is extended or adjusted under 35 U.S.C. 154(b) by 0 days.

(21) Appl. No.: 09/967,297

(22) Filed: Sep. 28, 2001

(65) Prior Publication Data

US 2003/0065258 A1 Apr. 3, 2003

(51) Int. Cl.[7] .............................................. A61B 5/055
(52) U.S. Cl. ........................ 600/410; 382/294; 382/131; 382/278
(58) Field of Search .......................... 600/410; 324/309, 324/307; 382/278, 128, 131, 294

(56) References Cited

U.S. PATENT DOCUMENTS

| 4,709,212 | A | * | 11/1987 | MacFall et al. | ............. | 324/309 |
| 5,717,618 | A | * | 2/1998 | Menkhoff et al. | .......... | 708/313 |
| 6,178,271 | B1 | * | 1/2001 | Maas, III | ..................... | 382/294 |
| 6,266,452 | B1 | * | 7/2001 | McGuire | .................... | 382/294 |
| 6,289,232 | B1 | * | 9/2001 | Jakob et al. | ................ | 600/410 |
| 6,292,683 | B1 | * | 9/2001 | Gupta et al. | ................ | 600/410 |
| 6,298,258 | B1 | * | 10/2001 | Heid et al. | .................. | 600/410 |
| 6,370,416 | B1 | * | 4/2002 | Rosenfeld | ................... | 600/410 |
| 6,448,771 | B1 | * | 9/2002 | Harvey et al. | .............. | 324/307 |

OTHER PUBLICATIONS

T. L. Davis, et al., "Calibrated Functional MRI: Mapping the Dynamics of Oxidative Metabolism," Proc. Natl. Acad. Sci. USA 95:1834–1839, 1998.

D. Li, et al., "Assessment of Myocardial Response to Pharmacologic Interventions Using an Improved MR Imaging Technique to Estimate T2* Values," AJR 172:141–145, 1999.

M. Solaiyappan and S. N. Gupta, "Predictive Registration of Cardiac MR Perfusion Images using Geometric Invariants," Proc. ISMRM. 3:2178, 1999.

C. M. Wacker, et al., "Changes in Myocardial Oxygenation and Perfusion Under Pharmacological Stress with Dipyridamole: Assessment Using T*2 and T1 Measurements," Magnet. Reson. Med. 41:686–695, 1999.

R. P. Woods, et al., "Rapid Automated Algorithm for Aligning and Reslicing PET Images," J. Comp. Ass. Tomog. 16(4):620–633, 1992.

* cited by examiner

*Primary Examiner*—Dennis W. Ruhl
*Assistant Examiner*—Barry Pass
(74) *Attorney, Agent, or Firm*—Quarles & Brady LLP

(57) ABSTRACT

The present invention is a method and apparatus for semi-automatically registering low signal to noise ratio relaxation-time images, with particular application to tracking motion in moving organs and quantifying myocardial perfusion reserve. For each image acquired in a time series, a corresponding high signal to noise ratio image is extrapolated from the collected data. The high signal to noise ratio images are registered to track motion, and the resulting registration data is copied onto the corresponding relaxation time image.

22 Claims, 5 Drawing Sheets

ANALYSIS OF CARDIC MR RELAXATION TIME IMAGES WITH APPLICATION TO QUANTIFYING MYOCARDIAL PERFUSION RESERVE INDEXES

STATEMENT REGARDING FEDERALLY SPONSORED RESEARCH OR DEVELOPMENT

This invention was made with U.S. government support awarded by the following agency: NIH HL03837. The U.S. government has certain rights in this invention.

The present invention relates generally to magnetic resonance imaging (MRI), and more particularly to a method and apparatus for tracking motion, such as anatomical movement, between MR images for efficient and effective MR image registration in blood oxygenation level dependent magnetic resonance imaging, and particularly for indexing myocardial perfusion reserve.

BACKGROUND

The ability to track motion in a time series of images is essential to a number of MRI applications, and particularly to applications involving imaging of, or within, moving organs. In these applications, it is important to be able to track motion not only to appropriately and accurately locate a region of interest, but also to apply motion artifact correction techniques. Motion artifact correction techniques are important in a number of applications including MR angiography (MRA) of coronary arteries; functional MR imaging (MRI) of brain physiology; and heart function monitoring to assess the severity and extent of damage in ischemic heart disease. Another important application in which motion tracking is required for proper MRI analysis is in myocardial perfusion imaging, which can be used to estimate the myocardial perfusion reserve, or blood flow through the heart.

Myocardial perfusion imaging is typically performed by injecting a contrast agent, such as gadolinium (or Gd-TPA), and obtaining a time series of data indicative of the kinetics of the contrast agent as it moves through the heart. While this process has proved successful in providing high signal to noise ratio (SNR) images for characterizing perfusion and perfusion reserve, there are certain disadvantages associated with contrast agent methods. Particularly, due to the need to inject an exogenous contrast agent, it is not possible to perform repeated studies within a short period of time using this method. Contrast agent methods, therefore, generally cannot be used to efficiently provide serial studies of heart conditions.

A promising alternative method of myocardial perfusion imaging is blood oxygenation level dependent (BOLD) MRI. In BOLD MRI, sensitivity to deoxyhemoglobin is used as a natural paramagnetic contrast agent to determine blood flow changes in the body, and exogenous contrast agents are therefore not required. Transverse relaxation-time (T2*) images, which have a signal intensity that is inversely related to deoxyhemoglobin concentration are acquired and analyzed for a patient in both a stressed and an unstressed state to determine changes in signal intensity. The changes in signal intensity correlate to changes in oxygenation level, and therefore provide a means for indexing the blood flow changes or myocardial perfusion reserve.

While BOLD MRI offers a number of advantages over previous methods of imaging myocardial perfusion by, for example, eliminating the need for an exogenous contrast agent and making repeated studies possible within relatively short time period, prior art methods of using BOLD MRI for myocardial perfusion analysis have proved to be relatively inaccurate. Critical inaccuracies relate to the inability to adequately register low SNR relaxation time images of moving bodies. Known pattern matching techniques such as least squares and cross-correlation techniques, have proven less than entirely effective when applied to these very low SNR relaxation time weighted images and particularly when applied to T2* images of moving bodies. When using BOLD MRI, therefore, a large portion or even all of the images are generally registered manually. This process is extremely time consuming and prone to operator error, thereby making BOLD MRI analysis impractical.

There remains a need, therefore, for a method and apparatus that can accurately and quickly register time series of relaxation-time images to track motion, and particularly for such a method and apparatus which is suited for use in myocardial perfusion imaging.

SUMMARY OF THE INVENTION

The present invention is a method and apparatus for using magnetic resonance imaging (MRI) techniques to register and analyze time series of relaxation-time images, and particularly for analyzing images of a moving body characterized by a significant degree of noise. Generally, in the method of the present invention, an anatomical image having a high contrast between the background and the region of interest, such as the myocardial region, is reconstructed in conjunction with each of a time series of relaxation-time images indicative of flow or motion of a body. Successive high contrast anatomical images are registered, or mathematically aligned, to accurately track motion of the body between successive images. The registration data can then be applied to the lower SNR relaxation-time images, and used to identify regions of interest for analysis, allowing for semi-automatic registration of the relaxation-time images.

In a preferred embodiment, the method of the present invention is used to derive a parameter characterizing the ability to augment tissue blood flow or oxygenation in response to stress using BOLD MRI, wherein the characterization preferably takes the form of an "index" illustrating the relative change in blood flow between a rest and a stressed state. The derived parameters can be used to index myocardial perfusion reserve, a measure of the ability of the heart to meet increased metabolic demand under stress. Here, a repeated series of transverse relaxation-time (preferably T2*) images are taken for each of a rest and a stressed state, thereby defining a time-series. Such images provide an indication of oxygenation levels in the heart, and can therefore be used to determine blood flow changes in the heart. However, due to signal intensity decay with time, transverse relaxation-time images generally have a low SNR. To locate the desired regions of interest in the collected T2* images, a second set of higher SNR images are acquired or constructed. These can be, for example, proton density images mathematically extrapolated for an echo time substantially equal to zero, providing a high contrast image wherein the background is substantially dark or black and the region of interest is substantially light or white. The high contrast images provide a relatively high definition, stable anatomical image of the body of interest for comparison purposes. These images can be analyzed efficiently with a number of known pattern matching techniques, and can be used to track motion of a region of interest at successive times. The known change in position can then be applied to the low SNR images to determine the position of the region of interest for analysis of the relaxation-time images, thereby providing a fast, semi-automatic analysis of the images which compensates for potential misregistration due to breathing and cardiac motion by utilizing higher contrast images in obtaining the registration data.

These and other objects, advantages and aspects of the invention will become apparent from the following description. In the description, reference is made to the accompanying drawings which form a part hereof, and in which there is shown a preferred embodiment of the invention. Such embodiment does not necessarily represent the full scope of the invention and reference is made therefore, to the claims herein for interpreting the scope of the invention.

DETAILED DESCRIPTION OF THE INVENTION

Figure 1:
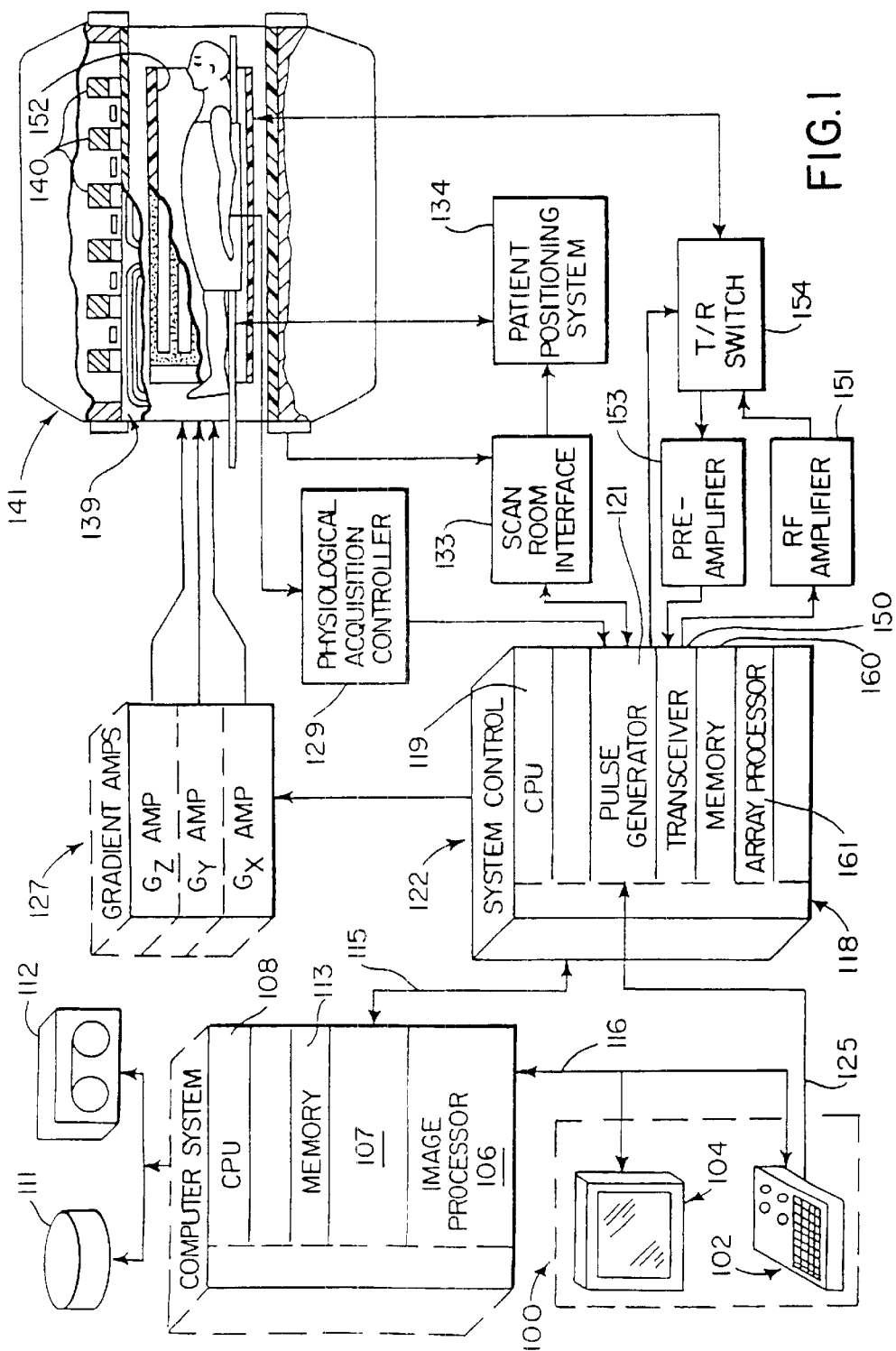
FIG. 1 is a block diagram of an MR system for providing the image data of the present invention.

Referring first to FIG. 1, the major components of one embodiment of an MRI system which can be used for performing the present invention are shown. The operation of the system is controlled from an operator console 100 which includes a keyboard and control panel 102 and a display 104. The console 100 communicates through a link 116 with a separate computer system 107 that enables an operator to control the production and display of images on the screen 104. The computer system 107 includes a number of modules which communicate with each other through a backplane. These include an image processor module 106, a CPU module 108 and a memory module 113, known in the art as a frame buffer for storing image data arrays. The computer system 107 is linked to a disk storage 111 and a tape drive 112 for storage of image data and programs, and it communicates with a separate system control 122 through a high speed serial link 115.

The system control 122 includes a set of modules connected together by a backplane. These include a CPU module 119 and a pulse generator module 121 which connects to the operator console 100 through a serial link 125. It is through this link 125 that the system control 122 receives commands from the operator which indicate the scan sequence that is to be performed. The pulse generator module 121 operates the system components to carry out the desired scan sequence. It produces data which indicates the timing, strength and shape of the RF pulses which are to be produced, and the timing of and length of the data acquisition window. The pulse generator module 121 connects to a set of gradient amplifiers 127, to indicate the timing and shape of the gradient pulses to be produced during the scan. The pulse generator module 121 also receives patient data from a physiological acquisition controller 129 that receives signals from a number of different sensors connected to the patient, such as ECG signals from electrodes or respiratory signals from a bellows. And finally, the pulse generator module 121 connects to a scan room interface circuit 133 which receives signals from various sensors associated with the condition of the patient and the magnet system. It is also through the scan room interface circuit 133 that a patient positioning system 134 receives commands to move the patient to the desired position for the scan.

The gradient waveforms produced by the pulse generator module 121 are applied to a gradient amplifier system 127 comprised of $G_x$, $G_y$ and $G_z$ amplifiers. Each gradient amplifier excites a corresponding gradient coil in an assembly generally designated 139 to produce the magnetic field gradients used for position encoding acquired signals. The gradient coil assembly 139 forms part of a magnet assembly 141 which includes a polarizing magnet 140 and a whole-body RF coil 152. A transceiver module 150 in the system control 122 produces pulses which are amplified by an RF amplifier 151 and coupled to the RF coil 152 by a transmit/receive switch 154. The resulting signals radiated by the excited nuclei in the patient may be sensed by the same RF coil 152 and coupled through the transmit/receive switch 154 to a preamplifier 153. The amplified NMR signals are demodulated, filtered, and digitized in the receiver section of the transceiver 150. The transmit/receive switch 154 is controlled by a signal from the pulse generator module 121 to electrically connect the RF amplifier 151 to the coil 152 during the transmit mode and to connect the preamplifier 153 during the receive mode. The transmit/receive switch 154 also enables a separate RF coil (for example, a head coil or surface coil) to be used in either the transmit or receive mode.

The NMR signals picked up by the RF coil 152 are digitized by the transceiver module 150 and transferred to a memory module 160 in the system control 122. When the scan is completed and an entire array of data has been acquired in the memory module 160, an array processor 161 operates to Fourier transform the data into an array of image data. This image data is conveyed through the serial link 115 to the computer system 107 where it is stored in the disk memory 111. In response to commands received from the operator console 100, this image data may be archived on the tape drive 112, or it may be further processed by the image processor 106 and conveyed to the operator console 100 and presented on the display 104.

Figure 2:
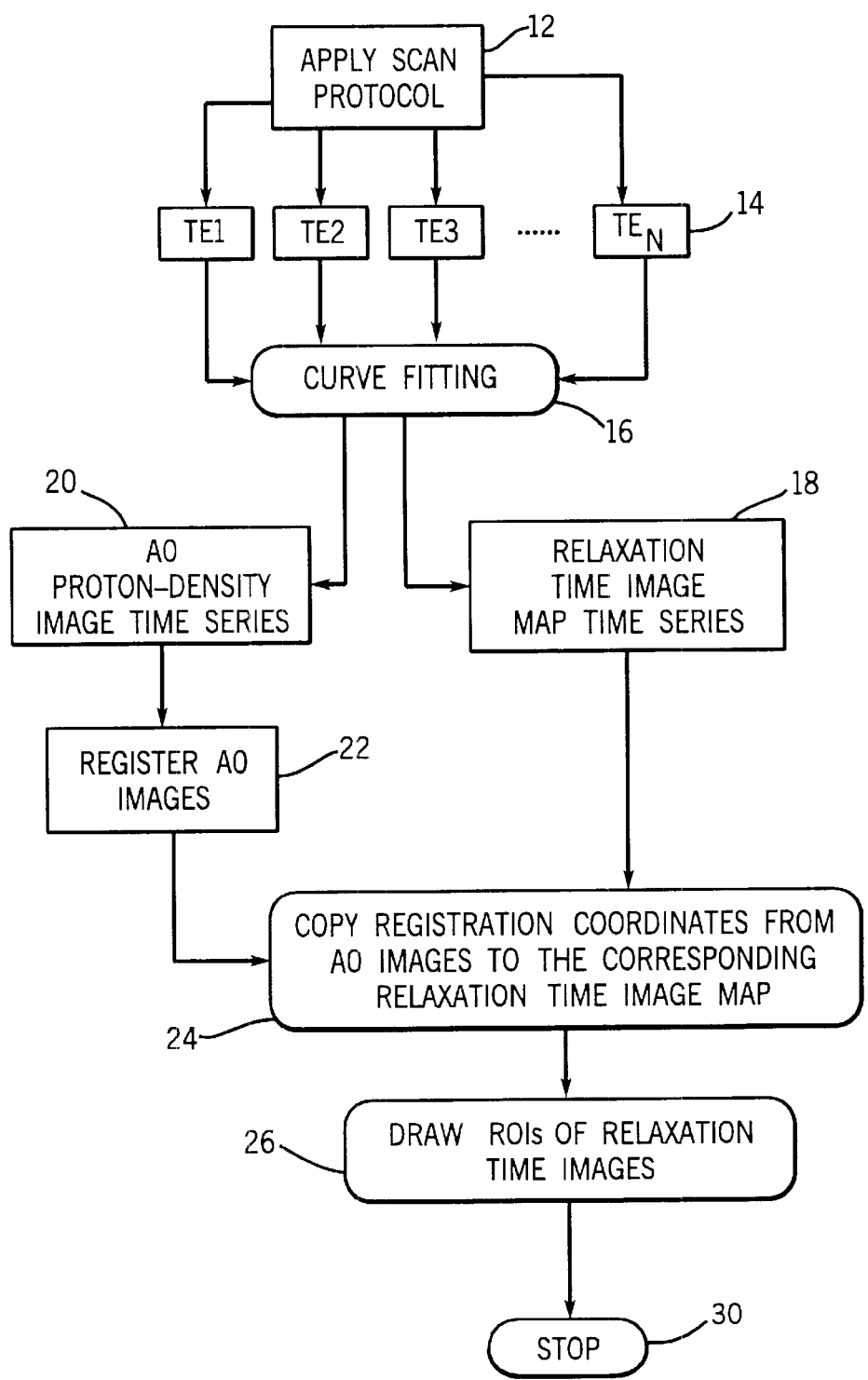
FIG. 2 is a flow chart illustrating a process for analyzing images provided in accordance with the present invention.

Referring now to FIG. 2, the method of the present invention generally involves the following steps: (1) applying a scan protocol 12 to a body to be imaged; (2) applying a curve fitting algorithm 16 to the acquired data to obtain relaxation-time images for each scan; (3) extrapolating the data to obtain a high contrast image 20 from the collected image data; (4) registering successive high contrast images to obtain registration data 22 which tracks motion or determines changes in position of the body being examined; (5) applying the registration results 22 to the lower SNR relaxation-time images to more accurately pinpoint a region of interest 18;

Initially, a series of relaxation time images is acquired by applying a scan protocol 12 through a pulse generator module and acquiring and processing the acquired data in a computer system, wherein the pulse generation module and computer can be, for example, the pulse generator module 121, image processor 106, and computer 107 as described above with respect to FIG. 1. As noted above, the pulse generator module 121 controls the timing, strength and shape of the RF pulses which are to be produced, and the timing of and length of the data acquisition window. These timing, strength, and shape factors can be selected by the user from the operator console 100, or stored as a program in the memory 13. The entire process including data acquisition, timing, processing and analysis of the data can be controlled from a program executed by the computer of the MRI system, or various components of the process can be controlled by an operator.

Depending on the selected scan protocol values, the user can acquire any of a number of types of types of known relaxation-time images, including T1, T2, and T2* images, in a manner known to those of skill in the art. The total time required to obtain relaxation-time images can be significant, generally in the range of one to two minutes, and therefore all of these types of images are affected by cardiac and respiratory motion and other noise produced in the body, as well as other system noise factors. As a result, all relaxation-time images can suffer from a suboptimal SNR. Consequently, when tracking motion of a body, relaxation-time images do not provide a sufficiently coherent image for analysis, even after pattern matching or other techniques are applied. To increase the accuracy of the computed relaxation-time image, the scan protocol 12 preferably acquires a plurality of images 14 at each of a plurality of echo times $TE_1$ through $TE_N$, such that a number of images can be used in constructing a fitted relaxation-time image, as described below. The number of images acquired can be selected by an operator based on the desired accuracy, the speed of the available equipment, and the amount of time required to maintain the subject under the scan.

When the scan protocol 12 is complete, the images 14 are processed by application of the computer 107 and/or image processor 106 as described above. A curve fitting algorithm 16 is applied to the images 14 acquired at the echo times $TE_1$ through $TE_N$ to construct the relaxation-time image 18. Curve fitting is also applied to the acquired data to extrapolate the proton density image 20, which is equivalent to the image acquired at an echo time TE substantially equal to zero. The curve fitting procedure 16 can comprise any of a number of known techniques including pixel by pixel curve fitting, log-fitting, and least squares fitting. For each relaxation-time image 18 acquired in the time series, the corresponding high contrast proton density image 20 is also extrapolated. The proton density images 20 provide a stable, high contrast image of internal organs, tissue, and skeletal structure, and can therefore be used to clearly indicate a region of interest.

As successive relaxation-time images 18 and high contrast images 20 are acquired, the high contrast images 20 are registered to track motion between successive images, and registration data 22 indicative of changes in the position of the body being imaged is acquired. A number of known techniques can be used to register the successive high contrast images, including pattern matching techniques such as cross-correlation and least squares methods. Preferably, however, motion is tracked using the automatic registration technique described in "Predictive registration of Cardiac MR Perfusion Images using Geometric Variants," M. Solaiyappan, S. N. Gupta, Proc. ISMRM, 2000, Denver, vol. 1 p. 37 which is hereby incorporated by reference for the explanation of this technique.

Registration data 22 is then mapped onto the acquired relaxation-time images 18 providing coordinates 24 to track motion in the low SNR relaxation-time image 18. Regions of interest 26 can be readily identified from the registration data 22, and therefore one or more regions of interest 26 can be tracked in each of the successive relaxation-time images 18.

In a preferred embodiment, the method of the present invention is used to analyze cardiac MR relaxation time images to derive registered time series data. The registered time series data can be used to index the myocardial perfusion reserve of a patient, or the blood flow change in the heart under stressed condition. The method employs blood oxygenation level dependent (BOLD) magnetic resonance imaging, which uses sensitivity to deoxyhemoglobin as an natural paramagnetic contrast agent to determine blood flow change in the body. Transverse relaxation-time (T2*) images, which have a signal intensity that is inversely related to deoxyhemoglobin concentration, are acquired and analyzed to determine changes in signal intensity. The changes in signal intensity correlate to changes in oxygenation level, and therefore provide a means for indexing myocardial perfusion reserve. High contrast proton density images acquired by extrapolating each image to an echo time of zero, as described above, provide a template for locating regions of interest and tracking motion during image acquisition.

Figure 3:
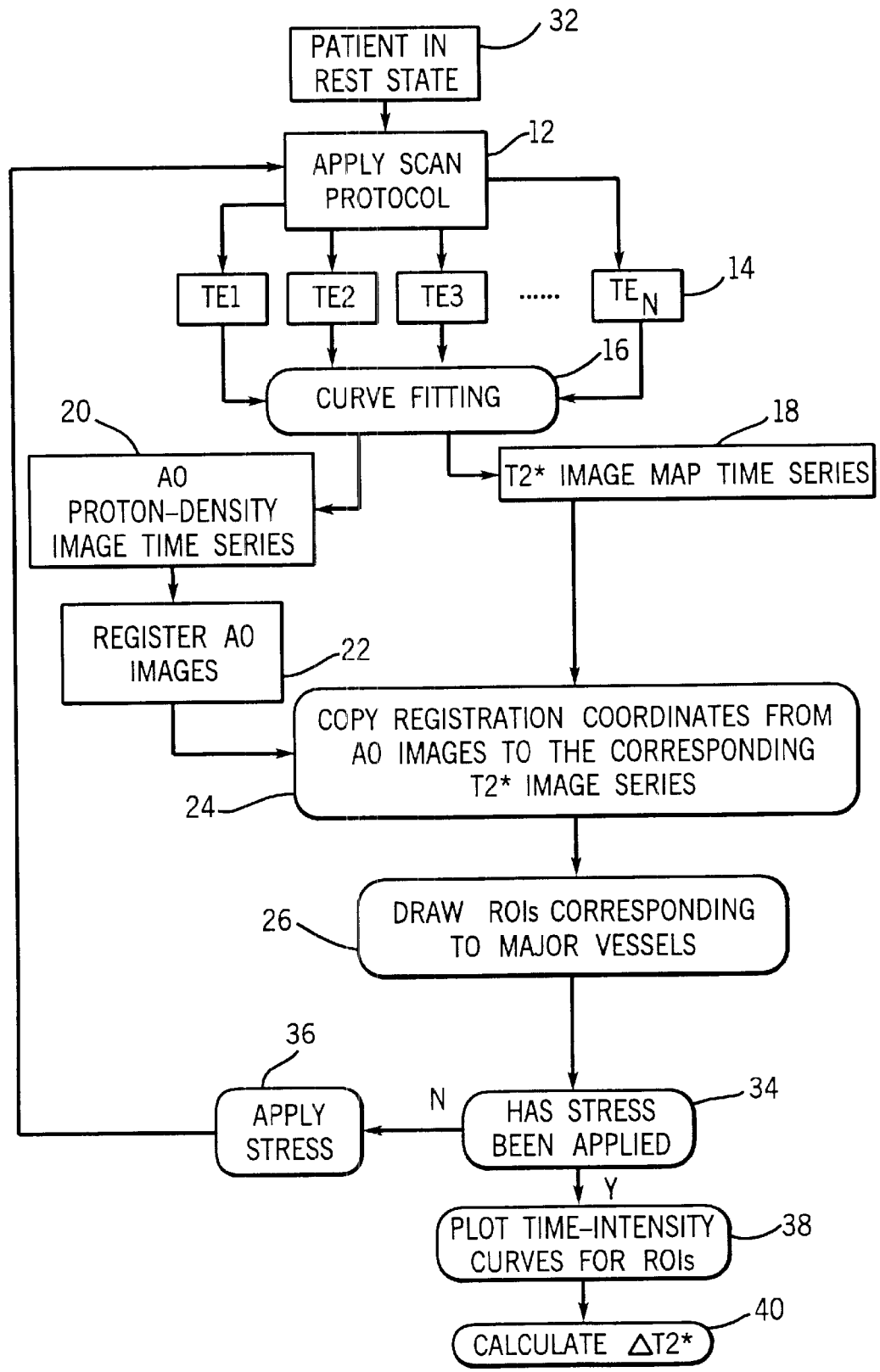
FIG. 3 is a flow chart illustrating a process for indexing myocardial perfusion reserve in accordance with the present invention.

Referring now to FIG. 3, in this embodiment, a first set of data is acquired while the patient is in a rest state 32. The first set of data provides a baseline oxygenation level indicative of blood flow-state in the heart in the rest state, and is used to analyze changes in blood flow as stress is applied. The image data for the baseline rest state 32 are acquired as described with reference to FIG. 2, wherein the relaxation-time image 18 is a T2* image. The scan protocol 12 is ECG-gated, or triggered on each heart beat, to minimize noise. As noted with respect to FIG. 2, a proton density image 20 is extrapolated for each acquired relaxation time image 18, and successive proton density images 20 are registered to provide registration data 22. The coordinates 24 are then mapped onto the relaxation-time images 18, and a region of interest 26 is located. For the myocardial perfusion application, the region of interest 26 may logically comprise the major heart vessel territories, and in particular the three principal vascular territories RCA, LAD and $LC_x$. The rest state data may be acquired as a single time point image, or multiple time points of data may be acquired to establish a more repeatable baseline. In either case, images are acquired successively at predetermined time intervals until a predetermined number of images are acquired.

When the predetermined number of images are acquired, a decision 34 is made whether to proceed to apply stress to the patient. This decision can be automated by providing a software-driven indicator to a user of the MRI system, or can be determined directly by a user following a procedure. If a set of data has not been acquired for the stress state, and acceptable baseline dataset has been acquired, then stress is applied to the heart of the patient to index the change in blood flow from the rest to the stressed state 36. The stressed state 36 is preferably induced through an injection of a pharmacological agent dipyridamole, which stresses the heart as an alternative to exercise. However, other pharmacological and physiological means for stressing the heart of a patient can be used, as will be known to those of ordinary skill in the art.

Once the heart is in a stressed state 36, the same ECG-gated T2* scan protocol 12 applied to acquire images in the unstressed condition 32 is applied, and a second set of data comprising a time series of T2* images 18 proton density images 20 and registration data 22 is acquired, as described above. Again, images are acquired until predetermined time series of images are acquired. Preferably, images are taken at seven or more echo times providing images $TE_1$ through $TE_7$. As noted above, however, the number of images acquired can be varied by the operator and will depend on the speed of the associated equipment, the desired accuracy of the result, and the amount of time considered appropriate for a patient to be subjected to the scanning procedure.

As noted above, changes in deoxyhemoglobin in the blood are manifested in T2* images by changes in signal intensity. Therefore, signal intensity versus time curves 38 are plotted over both the stressed and unstressed states in each of the defined regions of interest 26. The average rest state (baseline) and average stressed state (post-dipyridamole) signal intensity values are quantified from these plots. A quantitative BOLD parameter indexing the ability to augment tissue blood flow or oxygenation is then calculated as the maximum signal intensity change due to the effect of the dipyridamole divided by the average baseline value. This value is expressed as a percentage change in T2* (or 1/T2*) between the stressed and unstressed states 40 (%ΔT2*, or %ΔR2*) to provide a BOLD parameter indexing myocardial perfusion reserve.

Figure 4:
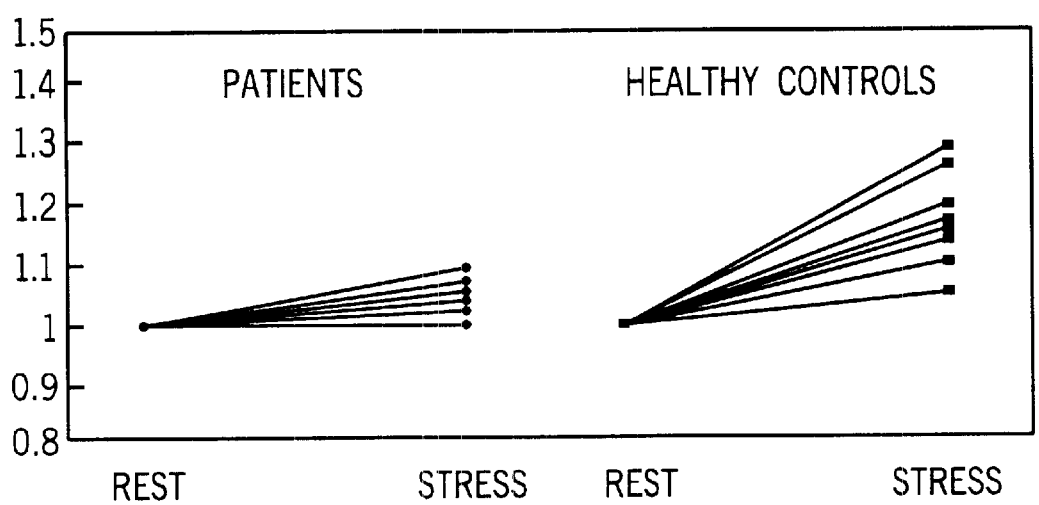
FIG. 4 is a graph illustrating the quantitative BOLD parameters for a group of healthy subjects and a group of patients suffering from hypertension.
Figure 5:
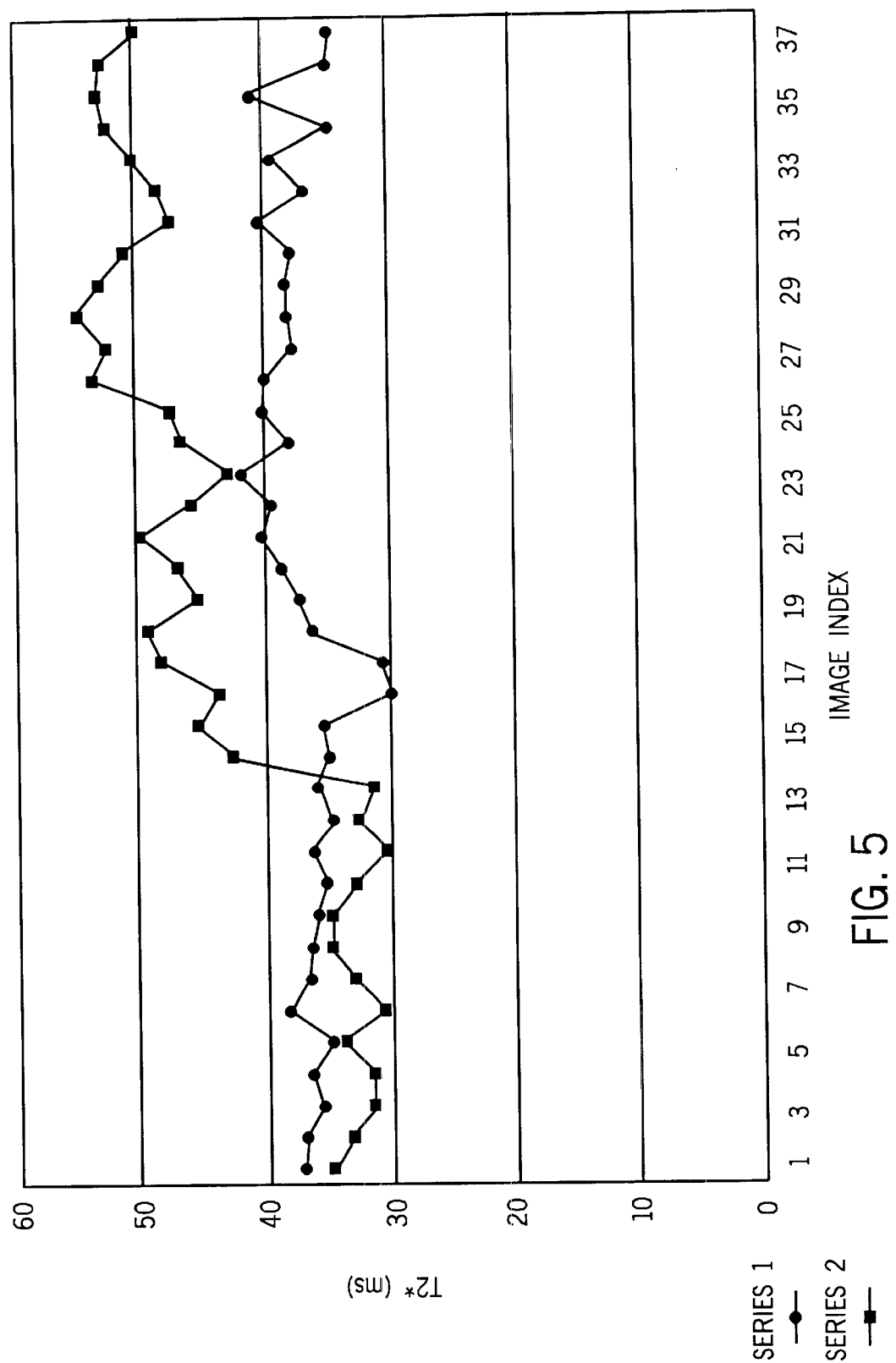
FIG. 5 is a graph illustrating the T2* signal intensity time series for a patient and a healthy subject acquired over baseline rest state and stressed state.

The described method was applied to ten patients having documented hypertension (blood pressure greater than 140 over 90) and having severe to moderate hypertrophy as defined by the echocardiographic LV mass criteria. As a comparison, the method was also applied to nine healthy controls having no history of hypertension, diabetes or heart disease. MR images were obtained using a Signa® 1.5 T system, with subjects placed supine and by using a single-channel surface coil. Cardiac short-axis, single slice, ECG-gated spoiled gradient echo datasets of nine images, with equally spaced echo time (TE) values over 2–26 ms, were acquired over a single breath hold. Saturation pulses were used to null the blood signal. Each scan protocol included 5 RF excitations, each followed by a nine-echo readout, applied during a 138 ms diastolic window of each cardiac cycle. Typical parameters were TR/α/RBW=28 ms/30°/+/−62.5 kHz, with matrix size of 256×120 and field of view 400 mm×400 mm. After acquisition of repeated data sets to establish a baseline, dipyridamole was administered via a peripheral vein (0.56 mg/kg total, over 4 minutes). Post-dipyridamole images were acquired approximately every minute for twenty minutes. Pulse rate and blood pressure were monitored. Total study time was approximately 40 minutes. A graph illustrating the data collected for both 8 healthy subjects and 6 patients suffering from hypertension are shown in FIG. 4. Here, the results have been normalized or indexed such that the value "one" represents the rest state blood flow, and the change in blood flow after stress is represented as a value of one or greater. A graph showing the normalized T2* signal intensity changes over the rest and stressed conditions for one healthy subject and one patient are shown in FIG. 5.

In the preferred embodiment, each dataset consisted of nine images ($TE_1$ through $TE_9$). The nine images were combined to generate a T2* relaxation-time image 18 using a pixel by pixel by fixed curve fitting algorithm 16 in which the correlation coefficient cut-off was established at 0.95, to minimize the inclusion of vessel voxels.

Although preferred embodiments have been shown and described, it will be apparent to one of ordinary skill in the art that a number of modifications could be made to the method and apparatus described without departing from the scope of the invention. For example, although a specific MRI system has been described, it will be apparent that a number of similar systems known to those of skill in the art could be employed in the present invention.

Furthermore, although a specific order for obtaining and processing images has been shown, it will be apparent that the acquisition of and processing of images can be performed in a number of different ways. For example, a time series of images can be acquired and processed when the acquisition is complete, images can be processed during acquisition of the time series of images, or certain processing functions can be performed during acquisition and others after acquisition is complete.

Additionally, although a specific embodiment of the present invention for use in indexing myocardial perfusion reserve has been shown and described, the present invention can be applied to a number of different applications in which time series of relaxation-time images are analyzed. The present invention is particularly suited for applications in which a moving body is analyzed. Examples include imaging of functioning of the kidneys, brain functional imaging, and other functional applications. Depending on the application, the number and type of relaxation-time images acquired can be modified to suit the application.

In addition, although a specific order for processing the images of the present invention has been shown and described, the use of registration data from the high contrast images can be correlated with the low SNR relaxation time images in a number of different ways. For example, as shown, registration from the high-contrast images is determined and then copied to the low SNR images. However, the regions of interest can be located in the high SNR images and these specific regions can be analyzed on the low SNR images. Other methods of employing the registration data from the high contrast template in coordination with the low SNR signals will be apparent to those of ordinary skill in the art.

It should be understood, therefore, that the methods and apparatuses described above are only illustrative and do not limit the scope of the invention, and that various modifications could be made by those skilled in the art that would fall under the scope of the invention. To apprise the public of the scope of this invention, the following claims are made:

What is claimed is:

1. A method for deriving registered time series data from low signal to noise ratio relaxation time images, and particularly of images affected by motion during long acquisition times, the method comprising the steps of:

acquiring a time series of relaxation time MR images;

extrapolating a high signal to noise ratio image from each of the time series of relaxation time MR images;

registering each of the successive high signal to noise ratio images to obtain registration data;

applying the registration data from each of the high signal to noise ratio images to the corresponding relaxation time MR images.

2. The method as defined in claim 1, wherein the step of acquiring a time series of MR images comprises applying a scan protocol including a plurality of echo pulses for acquiring a set of images for each of the time series of scans.

3. The method as defined in claim 2, further comprising the step of applying a curve-fitting technique to each set of images.

4. The method as defined in claim 3, wherein the high signal to noise ratio image is a proton density image extrapolated during the curve fitting process for an echo time substantially equal to zero.

5. The method as defined in claim 1, further comprising the step of mapping coordinates from the high signal to noise ratio image to the low signal to noise ratio image to align successive relaxation time MR images.

6. The method as defined in claim 1, further comprising the step of identifying a region of interest in the relaxation time MR image.

7. A method for performing blood oxygen level dependent magnetic resonance imaging to analyze oxygenation changes in a region of interest, the method comprising the following steps:

applying an MRI scan protocol to obtain a transverse relaxation time image of a body of interest at timed intervals to obtain a time series of images, the scan protocol including a plurality of echo pulses for acquiring a series of images for each scan, applying a curve fitting technique to the series of images acquired from each scan protocol to construct a transverse relaxation time image for the scan, and to extrapolate a proton density image of the body of interest at an echo time substantially equal to zero;

registering successive proton density images in the time series;

correlating the registration data to the corresponding T2* images;

identifying a region of interest on each of the T2* images; and analyzing a signal intensity of the images to determine oxygenation changes in the blood.

8. The method as defined in claim 7, further comprising the steps of acquiring a first time series of images in a rest state, and a second time series of images in a stressed state.

9. The method as defined in claim 7, wherein the step of registering comprises applying a least squares pattern matching technique.

10. The method as defined in claim 7, wherein the step of registering comprises applying a cross-correlation technique.

11. The method as defined in claim 7, wherein the step of correlating comprises mapping coordinates from the proton density image to the relaxation time image.

12. The method as defined in claim 7, wherein the step of acquiring a time series relaxation time images comprises acquiring a series of T2* images.

13. A method for analyzing regional myocardial perfusion reserve using blood oxygenation level dependent magnetic resonance imaging, the method comprising the following steps:

acquiring a first time series of relaxation time images indicative of blood flow-state in the heart when a patient is at rest;

acquiring a first plurality of high signal to noise ratio images indicative of the internal organs, tissue, and skeletal structure of the region being imaged, wherein each of the plurality of high signal to noise ratio images corresponds to one of the first plurality of relaxation time images;

registering successive images of the first plurality of high signal to noise ratio images;

mapping the registration data determined from the first plurality of high signal to noise ratio images to the corresponding first time series of MR images;

identifying a region of interest on each of the first time series of relaxation time images;

acquiring a second time series of relaxation time images indicative of blood flow-state in the heart when a patient is at stress;

acquiring a second plurality of high signal to noise ratio images indicative of the location of heart tissue, wherein each of the second plurality of magnitude images corresponds to one of the second time series of relaxation time images;

registering successive of the second plurality of high signal to noise ratio images;

mapping the registration data determined from the second set of high signal to noise ratio images to the corresponding image of the second time series of MR images;

identifying a region of interest on each of the second time series of MR images;

comparing a signal intensity from the first time series of images and the second time series of images to quantify myocardial perfusion reserve.

14. The method as defined in claim 13, wherein the first and second time series of relaxation time images are transverse weighted T2* images.

15. The method as defined in claim 13, wherein the steps of acquiring each of the first and second time series of relaxation time images further comprises the step of applying a scan protocol including a plurality of echo pulses for acquiring a plurality of images, and applying a curve fitting technique to the plurality of images.

16. The method as defined in claim 15, wherein the high signal to noise ratio images are proton density images extrapolated to an echo time of substantially zero.

17. The method as defined in claim 15, further comprising the steps of calculating oxygenation-state in the blood in the rest state and in the stress state as an inverse of the image signal intensity in both the rest and the stressed states.

18. The method as defined in claim 13, further comprising the step of plotting signal intensity versus time curves for the region of interest of each of the first and second set of relaxation time images.

19. The method as defined in claim 13, further comprising the steps of calculating a blood oxygenation level dependent (BOLD) parameter by identifying the maximum change in signal intensity in the second plurality of images, dividing this value by the average signal intensity value of the first plurality of images.

20. The method as defined in claim 13, further comprising the step of applying dipyridamole to the patient to induce the stressed state.

21. The method as defined in claim 13, wherein the step of registering comprises applying a pattern matching technique to successive proton density images.

22. The method as defined in claim 13, wherein the pattern matching technique is a least squares method.

* * * * *